(12) United States Patent
Grimes et al.

(10) Patent No.: US 11,211,458 B2
(45) Date of Patent: Dec. 28, 2021

(54) PHOTOCATALYTIC DEVICE BASED ON RARE-EARTH ELEMENTS: METHODS OF MANUFACTURE AND USE

(71) Applicant: FLUX PHOTON CORPORATION, Hackensack, NJ (US)

(72) Inventors: Craig A Grimes, Raleigh, NC (US); Kevin Kreisler, Hackensack, NJ (US)

( * ) Notice: Subject to any disclaimer, the term of this patent is extended or adjusted under 35 U.S.C. 154(b) by 0 days.

(21) Appl. No.: 16/445,789

(22) Filed: Jun. 19, 2019

(65) Prior Publication Data

US 2019/0386105 A1    Dec. 19, 2019

Related U.S. Application Data

(60) Provisional application No. 62/686,876, filed on Jun. 19, 2018.

(51) Int. Cl.
| | |
|---|---|
| *H01L 29/12* | (2006.01) |
| *B82Y 20/00* | (2011.01) |
| *H01L 29/06* | (2006.01) |
| *C07C 1/12* | (2006.01) |
| *B82Y 30/00* | (2011.01) |
| *B82Y 40/00* | (2011.01) |

(52) U.S. Cl.
CPC ............... *H01L 29/12* (2013.01); *C07C 1/12* (2013.01); *H01L 29/0676* (2013.01); *B82Y 20/00* (2013.01); *B82Y 30/00* (2013.01); *B82Y 40/00* (2013.01); *C07C 2523/10* (2013.01)

(58) Field of Classification Search
CPC ....... H01L 29/12; H01L 29/0676; C07C 1/12; C07C 2523/10; B82Y 20/00; B82Y 30/00; B82Y 40/00
USPC .......................................................... 257/9
See application file for complete search history.

(56) References Cited

U.S. PATENT DOCUMENTS

| | | | | |
|---|---|---|---|---|
| 8,721,923 | B2* | 5/2014 | Wong ..................... | B82Y 30/00 252/301.4 P |
| 9,306,090 | B2* | 4/2016 | Suto ................ | H01L 31/035218 |
| 2013/0266809 | A1* | 10/2013 | Nueraji ................... | B01J 27/24 428/402 |
| 2014/0076404 | A1* | 3/2014 | Tan ..................... | H01L 31/0264 136/263 |
| 2015/0136229 | A1* | 5/2015 | Suto ...................... | H01L 31/055 136/257 |
| 2019/0341217 | A1* | 11/2019 | Nojeh ..................... | H01J 35/14 |

* cited by examiner

Primary Examiner — Tu-Tu V Ho
(74) Attorney, Agent, or Firm — Dunlap Codding, P.C.

(57) ABSTRACT

The present invention relates to the design and fabrication of a device able to efficiently convert broad-spectrum electromagnetic radiation, including but not limited to microwave, millimeter wave, infrared, visible, and ultraviolet, into charge carriers, then separate and direct said charge carriers to promote photosynthetic or photocatalytic reactions, such as the photoconversion of $CO_2$ and water vapor to hydrocarbon fuels. Device fabrication requires intercalation of rare-earth ion containing crystallites, be they nanoparticles or quantum-dots, bound by an electrically insulating organic or inorganic shell, within a one-dimensional semiconducting material nanoarchitecture such as arrays of nanowires or nanotubes.

18 Claims, 6 Drawing Sheets

PHOTOCATALYTIC DEVICE BASED ON RARE-EARTH ELEMENTS: METHODS OF MANUFACTURE AND USE

FIELD OF THE INVENTION

The present invention relates to a photocatalytic device based on rare-earth elements intercalated within one dimensional (1D) semiconductor material nanoarchitectures of high interfacial surface area to enable the radiation-generated charges in the rare-earth ion containing crystallites, which would otherwise recombine, to tunnel through any charge transport-limiting organic or inorganic layer to reach the charge separating and transporting one dimensional (1D) nanoarchitecture

BACKGROUND OF THE INVENTION

The rapid increase in the level of atmospheric carbon dioxide, $CO_2$, is a matter of great concern with respect to unwanted heating of our planet and its environmental consequences. Recycling of carbon dioxide via conversion into high energy-content fuel suitable for use in the existing hydrocarbon-based energy infrastructure is an intriguing concept for achieving sustainable solar fuels and reducing atmospheric $CO_2$ concentrations, however this concept is realistically practical only if renewable energy sources are used for the thermodynamically uphill transformation.

Rare-earth elements, the fifteen lanthanides as well as scandium and yttrium, are known to broadly absorb electromagnetic radiation due to their unique electron orbital structure; notably, the filled $5p^66s^2$ orbitals overlap with the 4f orbital. Bound within an electrically insulating 'cage', either organic host matrices such as organic ligands bearing aromatic chromophores, or inorganic host matrices such as halides, oxides, oxyhalides, or oxysulfides, rare earth metal ions are known to demonstrate up-conversion (UC) properties, wherein two or more low energy photons are absorbed with the emission of a high-energy photon, as well as down-conversion (DC) properties with absorption of a high energy photon resulting in emission of one or more low energy photons. This nonlinear behavior is a consequence of the radiation-generated electrons and holes within the rare earth ions being 'trapped' about the ion by an electrically insulating shell, be it an organic or inorganic layer, and, having no immediate pathway for travel, instead undergo various time-dependent probabilistic atomic energy-level transitions to ultimately luminesce. J. Wang, N. He, Y. Zhu, Z. An, P. Chen, C. A. Grimes, Z. Nie, Q. Y. Cai, *Highly-luminescent Eu, Sm, Mn-doped CaS Up/Down conversion Nanoparticles: Application to Ultra-Sensitive Latent Fingerprint Detection and in vivo Bioimaging*, Chemical Communications 54 (2018) 591-594] report upconversion efficiencies of over 59%.

It is desirable to provide an improved photocatalytic device to use sunlight for transformation of $CO_2$ and water vapor to hydrocarbon fuels such as methane, ethane, or even higher order hydrocarbons in which the solar fuels reduce atmospheric $CO_2$ emissions and provide a viable means for the storage and transport of solar energy.

SUMMARY OF THE INVENTION

Rare-earth element containing compounds, such as but not limited to lanthanide doped nanoparticles or quantum-dots, known to absorb broad-spectrum radiation due to their over-lapping electron orbitals, are intercalated within one-dimensional (1D) semiconductor material nanoarchitectures of high interfacial surface area, such as assemblies or arrays of semiconducting nanowires or nanotubes. The rare-earth ion containing crystallites, be they nanoparticles or quantum-dots, are bound in a shell-like manner by an electrically insulating organic or inorganic layer, however the nanoscale proximity of the charge-separation interface enables the radiation-generated charges in the rare-earth ion containing crystallites, which would otherwise recombine, to tunnel through any charge transport-limiting organic or inorganic layer to reach the charge separating and transporting 1D nanoarchitecture, and thus be made available to do useful work in photocatalytic reactions including, but not limited to, water-splitting, and photoreduction of $CO_2$ to hydrocarbon fuels such as methane or ethane.

The photocatalytic device is composed in part of crystallites, quantum-dots or nanoparticles that contain one or more rare earth ions, compounds notable for their ability to absorb broad spectrum radiation and, due to their extended photo-generated-charge lifetimes, their intrinsically nonlinear upconversion and down-conversion properties. These crystallites, nanoparticles or quantum-dots, herein referred to as nanoparticles, are intercalated within one dimensional (1D) semiconductor nanoarchitectures such as arrays of nanowires or nanotubes. Intercalation of the rare earth ion containing nanoparticles within such a material nanoarchitecture acts to quench, in part or whole, the luminescent pathways, for the excitons generated by the absorbed radiation are able to reach the surface of the proximate semiconducting one dimensional (1D) material nanoarchitecture, and there charge polarities are separated. Once separated, the charges are available to promote catalytic or synthetic reactions.

The photocatalytic device of the present invention utilizes a one-dimensional (1D) material nanoarchitecture, such as semiconducting nanowire or nanotube arrays, into which broad spectrum radiation absorbing rare earth ion containing crystallites, be they nanoparticles or quantum-dots, generally recognized as being about 1 nm to about 100 nm in diameter, are intercalated; the immediate proximity of the 1D nanostructures allows the radiation-generated excitons to tunnel through their electrically insulating 'cages' to rapidly reach the 1D material nanoarchitecture. The electrons-holes are separated at the interface with the 1D material nanoarchitecture, and subsequently transported to facilitate desired photocatalytic or photosynthetic reactions.

The invention will be more fully described by reference to the following drawings.

DETAILED DESCRIPTION OF THE INVENTION

Figure 1:
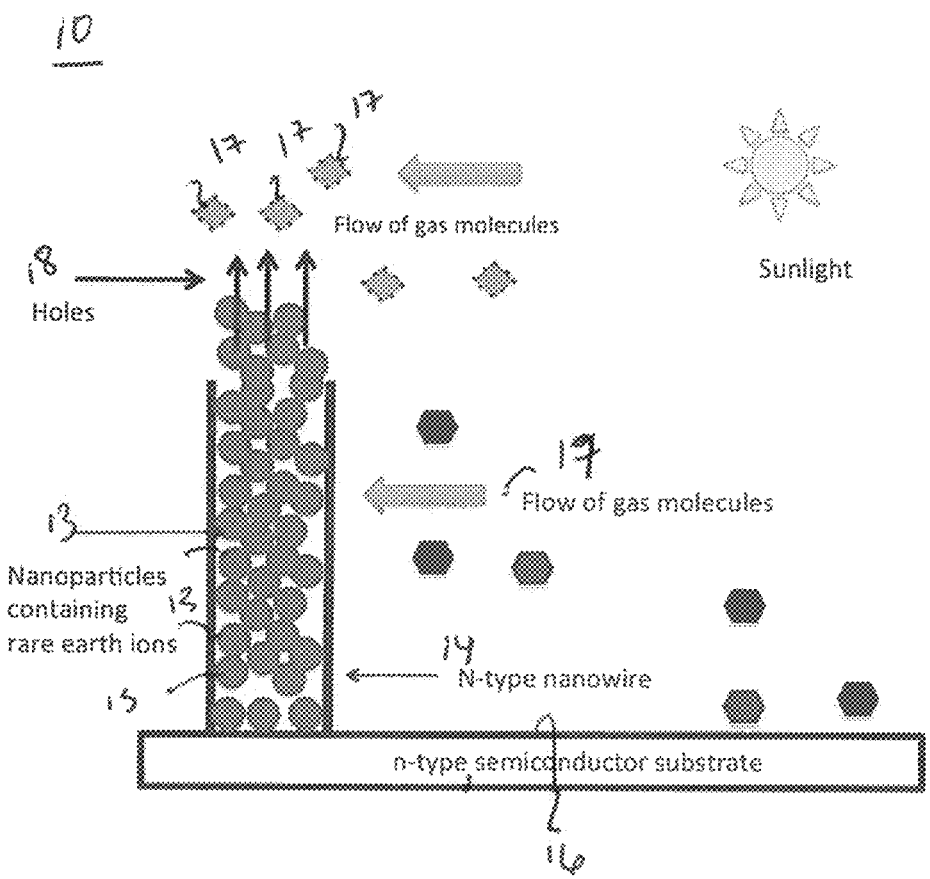
FIG. 1 is a schematic diagram of a photocatalytic device in accordance with the teachings of the present invention.

Reference will now be made in greater detail to a preferred embodiment of the invention, an example of which is illustrated in the accompanying drawings. Wherever possible, the same reference numerals will be used throughout the drawings and the description to refer to the same or like parts.

Having summarized the invention, the invention may be further understood by reference to the following detailed description and non-limiting examples.

FIG. 1 is a schematic diagram of one implementation of photocatalytic device 10. Rare-earth ion containing nanoparticles 13 are intercalated within nanowire 14 grown from substrate 116. Nanowire 14 can be a ntype nanowire. Substrate 16 can be a n type substrate. The rare-earth ion containing nanoparticles absorb radiation, which can include but is not limited to infrared, visible, and ultraviolet wavelengths, in turn generating electrons and holes. The electrically insulating (organic or inorganic) shell 15 about nanoparticles 13 would prevent, in and of itself, separation of the photogenerated electrons and holes; the electrons and holes, after a time, having nowhere else to go and possibly after going through either up or down-conversions in energy, recombine. Given the local proximity of nanowires 14 the electrons are able to tunnel through the electrically insulating barrier, and so the radiation generated electrons and holes are separated.

As depicted in FIG. 1 the electrons are free to travel along the length of both nanowire 14 and substrate 16 from which they are grown, where they are available to react or reduce with passing gas molecules 17. Within the rare earth ion containing nanoparticles 14 there becomes a surplus of holes 18, which also become available to react with or passing gas molecules 17.

The described photocatalytic device is not limited to a specific rare earth material or combination thereof. It is well known that rare earth containing nanoparticles absorb radiation, anything from microwave to X-rays, and in turn generate electron-hole pairs. Encompassed by an electrically insulating shell the charges are bound near the ion, with such extended lifetimes they frequently up or down-transition in energy, ultimately recombining, to luminesce, up to hours later. Intercalated within a one dimensional (1D) semiconductor material architecture radiation generated charges, rather than being held in a meta-stable state for hours where they are free to under go a host of energy transitions that ultimately lead to luminescence, would be rapidly separated and thus become available to promote catalytic or synthetic reactions.

In the present invention excitons generated within rare earth ion containing nanoparticles, which possess extended lifetimes, can be separated and collected before they undergo recombination transitions, and once collected readily transported to a surface where they can react with passing gas molecules. It has been found that to achieve this, due to the electrically insulating 'cage' that surrounds the rare earth ions, such as oxygen atoms, for example, it is desirable to intercalate the rare earth ion containing nanoparticles within a high-surface area one-dimensional (1D) exciton-transporting device geometry In such a material architecture the rare earth-ion generated excitons are never more than a few nanometers away from a charge-separating interface which, in turn, promotes exciton tunneling from the rare earth ions through their electrically insulating 'cages' to the interpenetrating on dimensional (1D) semiconductor material nanoarchitecture.

Figure 2:
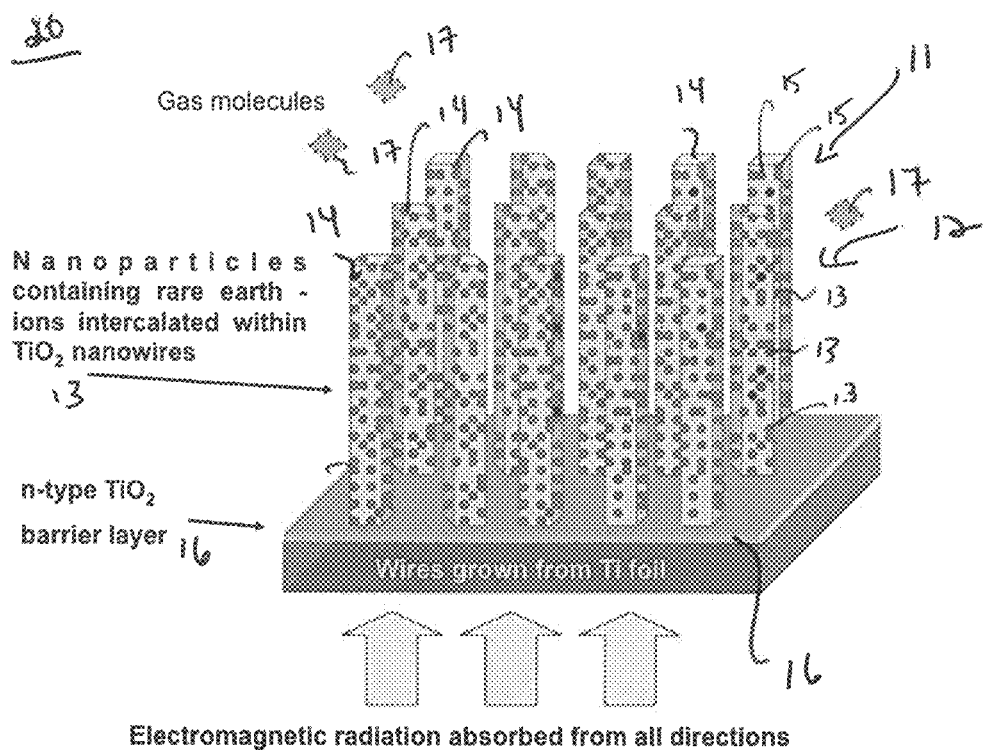
FIG. 2 is a schematic diagram of a photocatalytic device including an n-type $TiO_2$ nanowire array is intercalated with rare earth ion containing nanoparticles that are enclosed by an electrically insulating shell.

Referring to FIG. 2, is a schematic diagram photocatalytic device 20 including one dimensional (1D) nanoarchitecture 11 comprising nanowire array 12. Nanowire array 12 comprises a plurality of nanowires 14. Nanowires 14 are intercalated with rare earth ion containing nanoparticles 13. Example nanoparticles can include crystallites, quantum-dots, or nanoparticles Spacing between nanowires 14 within nanowire array 12 can be less than 10 μm facilitating charge collection from the intercalated material of nanowires 14. The length of the nanowires 14 can range from nanometers to centimeters, with longer wires enabling the fabrication of correspondingly thicker exciton scavenger devices that allow for more complete absorption of incident radiation. In one embodiment, the length of nanowires 14 is in a range of about 10 nm to about 1000 mm. The diameter of nanowires 14 can be in the range of about 5 nm to about 35 nm. It has been found that n array of smaller diameter wires results in higher interfacial surface area, however unless single crystal smaller diameter wires will be of higher electrical resistance. It will be appreciated that in accordance with the teachings of the present invention nanowires 14 can have various shapes including nanorods, nanotubes or other shapes such as for example nanofeathers or elongated ellipses. Nanoarchitecture 11 can be an or disordered, randomly oriented array of features selected from various shapes such as for example. nanowires, nanorods, nanotubes and nanofeathers.

Nanowires 14 can be grown from surface 16. For example, surface 16 can be a Ti foil. Excitons from nanowires 14 can be received at electrical contact 20. The small wire-to-wire spacing and the long exciton lifetimes, on the order of milliseconds, enables the excitons to tunnel through the electrically insulating 'cage' to reach nanowires 14, where they are then transferred to electrical contact 20.

In FIG. 2, the wire composition of nanowires 14 chosen for the example is $TiO_2$, an electron-transporting n-type semiconductor. In operation of photocatalytic device 10, the electron-hole pairs generated by the 'caged' rare earth ions upon absorption of radiation will be separated due to the ability of the electrons to tunnel through the electrically insulating cage, that is but a few atomic layers thick, to reach nanowire 14 Once in nanowire 14, the electrons can readily travel within any contiguous n-type materials to reach and react with any passing gas molecules 17. Excess of radiation-generated holes 18 will accumulate in nanoparticles 14 that will be available to react with passing gas molecules 18.

The rare earth ions can be bound within an organic host matrix comprising organic ligands bearing aromatic chromophores. The rare earth ions can be bound within an inorganic host matrix, the matrix being comprised of halides, oxides, oxyhalides, or oxysulfides. Radiation absorbed by the rare earth ion containing material can possess a wavelength from between 0.01 μm and 300 cm. Rare earth ions can be comprised of one or more of the following elements: lanthanum, cerium, praseodymium, neodymium, promethium, samarium, europium, gadolinium, terbium, dysprosium, holmium, erbium, thulium, ytterbium, lutetium, scandium, or yttrium. Rare earth ion containing material can be tuned to achieve either broad spectrum radiation absorption, the absorption of a specific wavelength, or the absorption of a specific band of wavelengths. Charge generation capabilities of the rare earth ion containing material can be adjusted through appropriate elemental doping. The rare earth ion containing material can contain one or more nonmetals selected from the group consisting of B, C, K, Ca, Na, F, I, P, S and mixtures The rare earth ion containing crystallites, quantum-dots, or nanoparticles can include one or more co-catalysts which are deposited on one or more surfaces of the device wherein the co-catalyst is selected from the group consisting of graphene, boron nitride, Ag, As, Au, Bi, Cd, Co, Cu, CuO, $Cu_2O$, Fe, Ga, Ge, In, Ir, Ni, Pb, Pd, Pt, Rh, Sb, Si, Sn, Ta, Tl, W, Zn or mixtures thereof. The rare earth ion containing crystallites, quantum-dots, and/or nanoparticles can be in contact with graphene or boron nitride, by which charge separation is facilitated. It is recognized in accordance with the teachings of the present invention that the exciton-transferring properties of the rare earth ion containing materials can be tailored, as necessary, through material composition and synthesis technique. So too the propensity of the charges to leave the 'caged' rare earth ions for that of the 1D charge transporting architecture can be adjusted through composition of either one dimensional (1D) nanoarchitecture 11, or the rare earth ion containing nanoparticles 13. The one dimensional (1D) nanoarchitecture 11 can be composed of any semiconductor material including for example, silicon, zinc oxide, tin oxide, niobium oxide, vanadium oxide, copper oxide, titanium oxide, GaN, GaAs, gadolinium phosphide, tungsten oxide, tantalum, strontium oxide and iron oxide. The composition of one dimensional (1D) nanoarchitecture 11 can be chosen to best match that of the rare earth ion containing nanoparticles 13 to ensure maximum radiation absorption and exciton collection. For example, nanowires 12 can be $TiO_2$ nanowires.

The interpenetrating one dimensional (1D) nanoarchitecture 11 is vital to operation of photocatalytic device 10 operation as the directions of exciton separation and radiation absorption are generally orthogonalized. While excitons are collected across a distance of but a few tens of nanometers, the length or thickness of one dimensional (1D) nanoarchitecture 11, be it wires or tubes or other shapes such as feathers or elongated ellipses, into which the rare earth ion containing nanoparticles 13 are intercalated, can range from microns to tens of mm in length allowing for greater absorption of incident radiation.

Photocatalytic device 10 can include any suitably rare earth ion containing nanoparticle 14 enclosed within an electrically insulating shell 15. There is considerable flexibility to the one-dimensional exciton collecting and transporting architectures that might be used in exciton scavenger device 10, both in the geometrical features, be they wires, tubes, rods, feather-shaped, plate-shaped and the like, and in their semiconducting properties, either n-type or p-type, and of any general semiconductor compositions, for example silicon, GaN, GaAs, gadolinium phosphide, tungsten oxide, tantalum oxide, zinc oxide, titanium oxide, copper oxide, strontium oxide, iron oxide, and the like. Given a specific radiation absorbing exciton generating rare earth ion containing nanoparticle 13, the composition of the intercalating one dimensional (1D) charge transporting architecture can be chosen to provide optimal power conversion efficiency.

Figure 3:
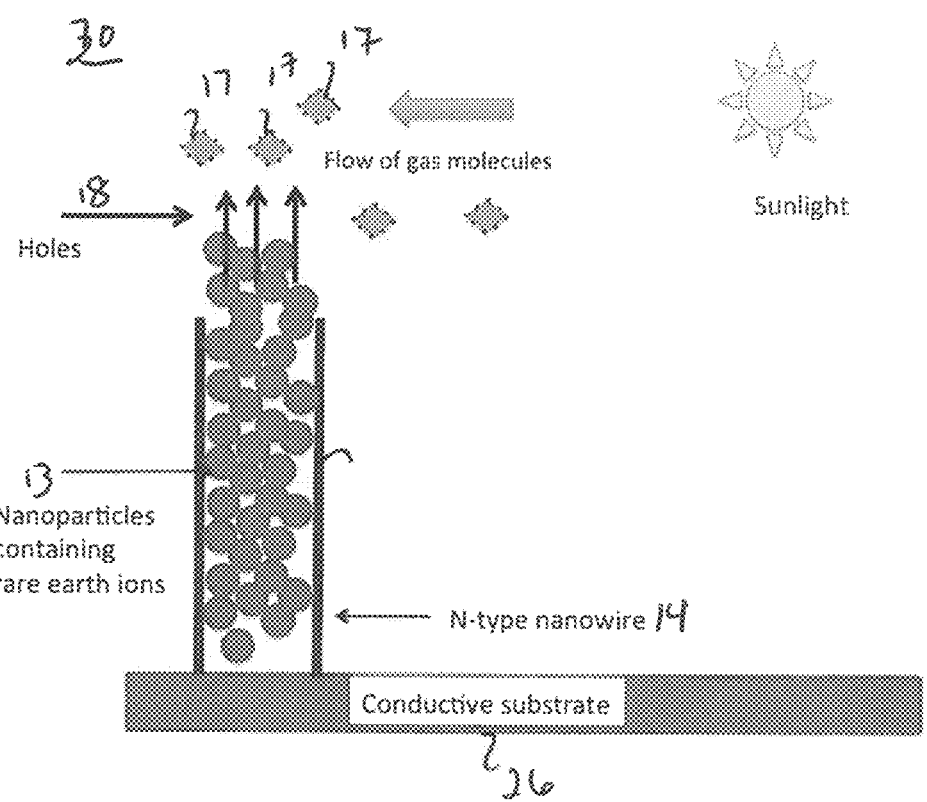
FIG. 3 is a schematic diagram of photocatalytic device in which n-type nanowires have been grown atop a conductive metal substrate.

FIG. 3 is a schematic diagram of photocatalytic device 30 including conductive substrate 26. Substrate 26 is formed of metal. Electrons generated within the rare earth ion containing nanoparticles 13 will tunnel through the electrically insulating layer, or shell 15, that surrounds nanoparticle 13 to reach nanowire 14. If the underlying substrate 26 is grounded, electrons traveling along nanowire 14 to reach substrate 26 will be removed from photocatalytic device 10. In the relative absence of electrons, holes 18 in nanoparticles 13 will accumulate, pass from one nanoparticle 13 to another nanoparticle 13 to reach the surface and there react with passing gas molecules 17.

In this case n-type nanowires 14 have been grown atop a conductive metal substrate 26. Suitabe examples include nanowires 14 of ZnO atop substrate 26 of zinc foil, or a nanotube replacing nanowire 14, the nanotube being formed of $TiO_2$ from substrate 26 of Ti foil. Nanowires 14 are intercalated with nanoparticles 13 containing rare earth ions of suitable composition. Electrons 19 generated within the nanoparticles 13 will tunnel through the electrically insulating layer or shell 15, that surrounds nanoparticle 13 to reach the n-type nanowire 14. If the underlying substrate 26 is grounded, electrons traveling along nanowire 14 that reach substrate 26 will be quenched. In the relative absence of electrons, holes 18 in nanoparticles 13 will accumulate, pass from one nanoparticle 13 to another nanoparticle 13 to reach the surface and there react with passing gas molecules 17. If the substrate 26 is not electrically grounded, but rather allowed to float, accumulated electrons will raise electrical potential and so achieve a specific relative balance in the availability of electrons and holes 18 to chemical reactions.

Figure 4:
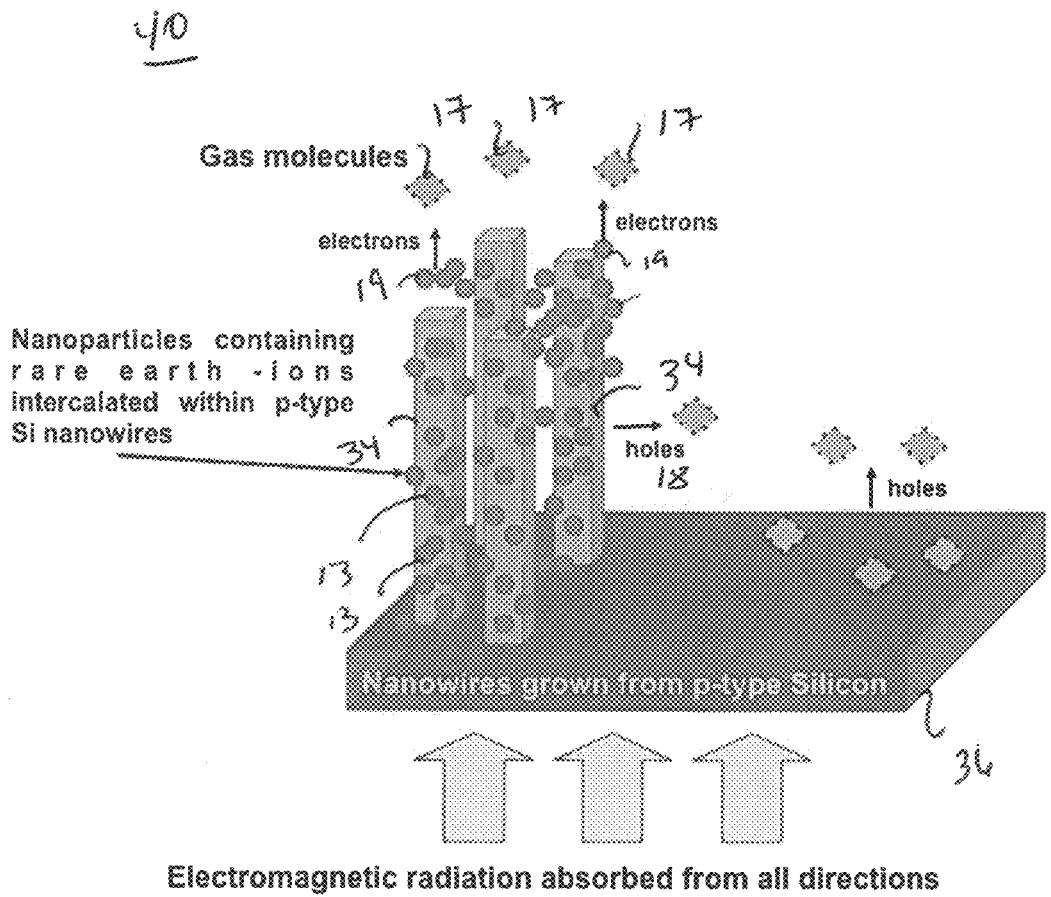
FIG. 4: is a schematic diagram of photocatalytic device of a photocatalytic device.

It is recognized in accordance with the teachings of the present invention that the charge separation and transport properties of the device can be tailored, as necessary, through material composition. For example, with reference to FIG. 4, photocatalytic device 40 is comprises substrate 36. Substrate 36 can be formed of a p-type silicon wafer. Nanowires 34 can be formed of semiconductor p-type silicon grown from substrate 36 Nanowires 34 can be intercalated with nanoparticles 13 containing rare-earth ions. The spacing between nanowires 34 is so small, on the order of a few nanometers to tens of nanometers, and the exciton lifetimes within nanoparticles 13 so long, that holes 18 are able to tunnel from the 'caged'—rare earth ion containing nanoparticles 13 to nanowires 34. Holes 18 collected by nanowires 34 formed of p type silicon are free to pass throughout the underlying substrate 36 formed of a p-type silicon wafer allowing, in flow-through reactor designs, for spatial separation of reactions.

Figure 5:
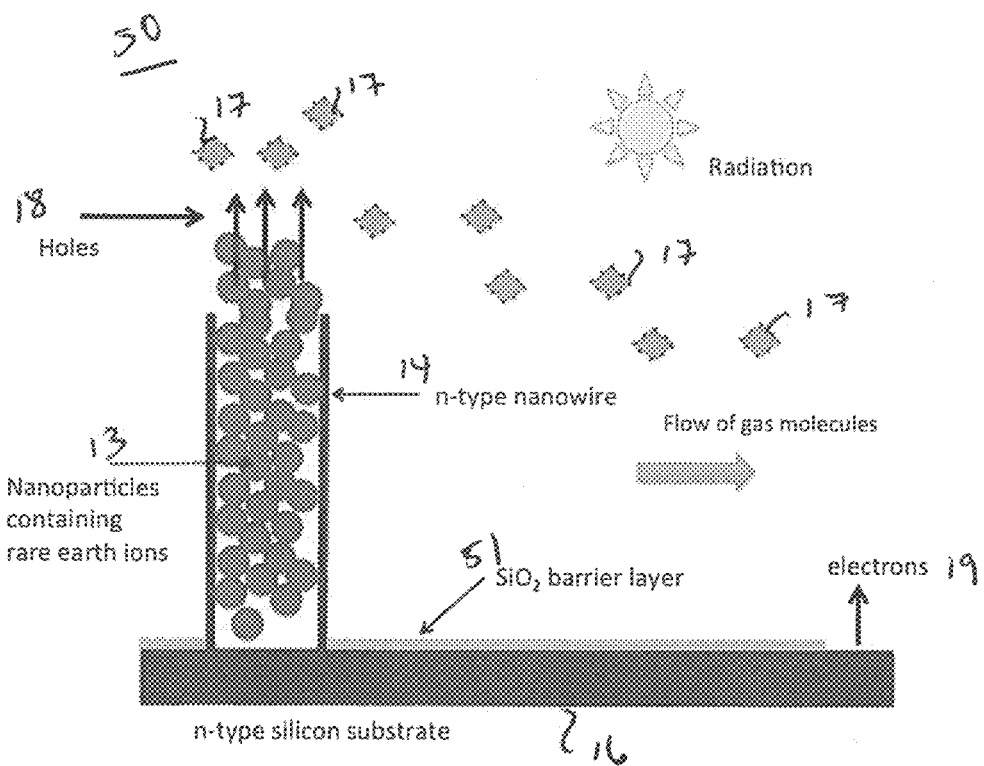
FIG. 5: is a schematic diagram of photocatalytic device implementation.

FIG. 5 is a schematic diagram of photocatalytic device 50. SiO2 barrier layer 51 is formed on substrate 16. Electrons 19 generated in the rare earth ion containing nanoparticles 13, transfer to nanowires 14 and then can either react with passing gas molecules 17 in contact with nanowires 14, or react with gas molecules 17 at a location spatially distant from nanowires 14 where substrate 16 is again exposed to the ambient.

Figure 6:
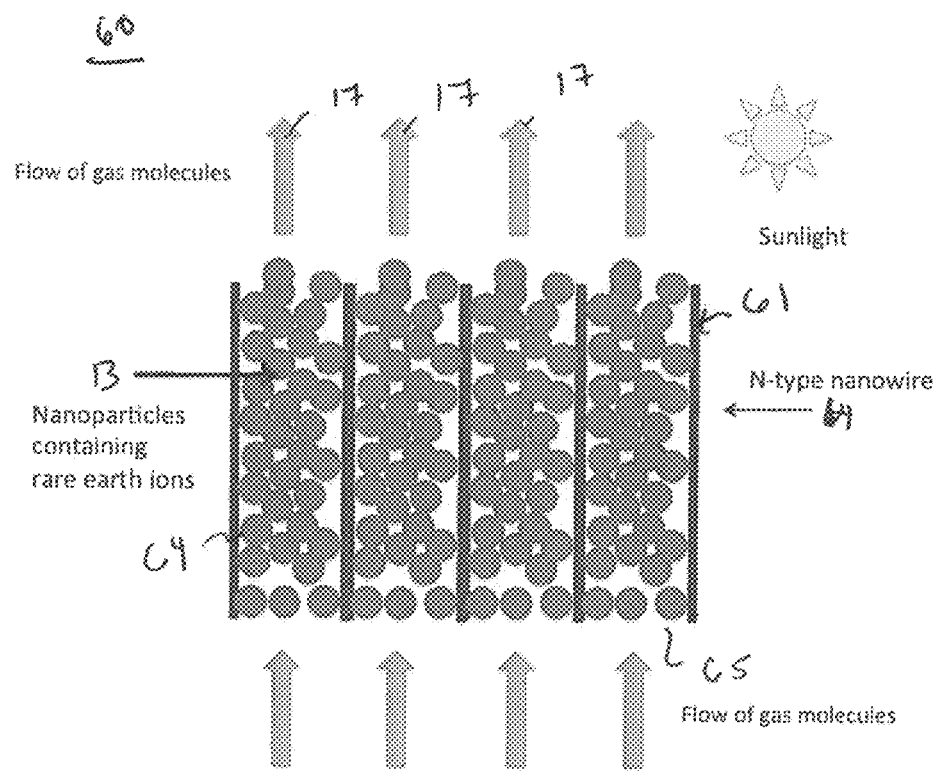
FIG. 6: Is a schematic diagram of photocatalytic device including a flow-through photocatalytic membrane, in which rare earth ion containing nanoparticles are intercalated within a free-standing porous 1D material architecture.

FIG. 6 is a schematic diagram of photocatalytic device 60. Rare earth ion containing nanoparticles 13 have been intercalated within nanotube array 61 comprising a plurality of nanowires 64. Nanowires 64 can be n type nanowires. Bottom 65 of nanotube array 61 has been removed to make a flow-through membrane. Nanotubes of smaller pore size, in particular pore diameters ranging from about 1 nm to about 60 nm, can provide more surface area for reaction.

To optimally promote desired photocatalytic or photosynthetic reactions the one dimensional (1D) material architecture can be composed of any semiconductor including silicon, zinc oxide, tin oxide, niobium oxide, vanadium oxide, copper oxide, titanium oxide, and iron oxide, and so on, to name some examples. While radiation-induced charges are separated and collected across a distance of but a few tens of nanometers, the length or thickness of the one dimensional 1D nanoarchitecture, be it wires or tubes or other shapes such as feathers or elongated ellipses, into which the rare earth ion containing nanoparticles are intercalated, can range from microns to several tens of mm in length allowing for greater absorption of incident radiation without sacrificing charge-collection properties.

The devices, as taught, can include any suitably 'caged' rare earth ion containing nanoparticles. There is considerable flexibility to the one-dimensional charge collecting and transporting architectures that might be used, both in the geometrical features, be they wires, tubes, rods, feather-shaped, plate-shaped and so on, and in their semiconducting properties (e.g. gadolinium phosphide, tungsten oxide, tantalum oxide, zinc oxide, titanium oxide, copper oxide, strontium oxide, graphene, graphene oxide, and so on). It is recognized that if the one dimensional (1D) material architecture is made of a semiconductor, that this semiconductor can either be n-type, for example titanium dioxide, or p-type, for example copper oxide, as desired depending upon the properties of the rare earth ions, their host, and whether the desired chemical reactions are facilitated by the presence of electrons, holes, or both.

Figure 7:
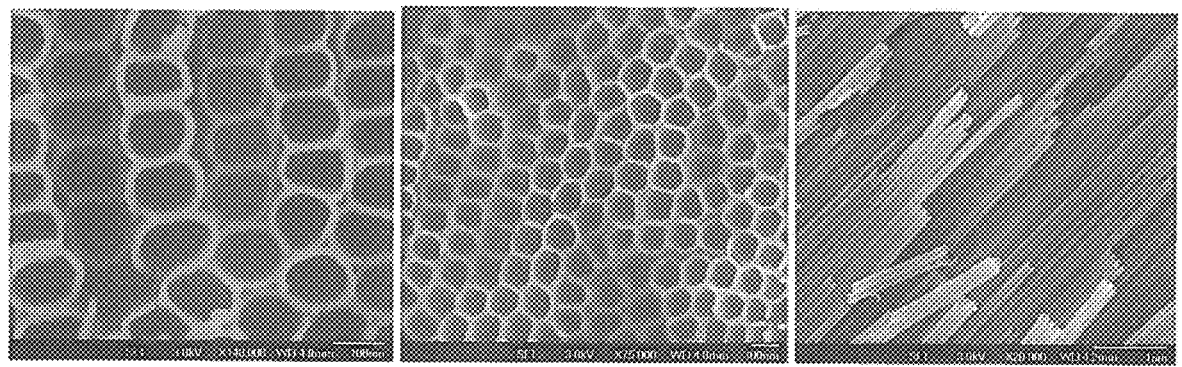
FIG. 7A-7C: Is a schematic diagram of $TiO_2$ nanotube arrays grown by anodization of Ti foil.

$TiO_2$ nanotube array films, illustrative images of which are shown in FIGS. 7A-7C, made by anodization of Ti foil in a fluorine-containing electrolyte, are an illustrative example of a 1D material architecture well suited for use within said rare earth one dimensiona (1D) photocatalytic devices. With respect to the nanotubes, using sol gel techniques, for example, or an electrodeposition technique, the tubes can be readily intercalated with the rare earth containing nanoparticles. Ordered, but so too dis-ordered arrays of nanoscale architectures such as wires or tubes, feather-like structures, disks, plates, and so on, can potentially be utilized in photocatalytic devices 10; the specific shapes can and do vary so long as the overall nanoscale architecture is one of high surface area, into which the rare earth containing nanoparticles 13 can be intercalated, and which supports rapid charge transfer. The work functions of the materials, and the materials themselves, can be chosen to promote a specific directional flow of photogenerated charge to optimally promote specific chemical reactions. Crystallinity of components of photocatalytic device 10 can be improved by exposure to an annealing step.

While the specific compositions can be varied, the key design parameter is the intercalation of rare earth ion containing nanoparticles within a charge-transporting 1D semiconductor material nanoarchitecture so that the radiation generated charges, rather than be left within the nanoparticle to, ultimately, recombine, as is known due to the electrically insulating shell that surrounds such nanoparticles, are separated and collected and thus made available to promote one or more chemical reactions.

It is understood that the rare earth containing nanoparticles can be synthesized using a variety of techniques, for example sol-gel, electrodeposition, microemulsion, atomic layer deposition, hydrothermal synthesis, microwave-assisted hydrothermal synthesis, dip-coating, and the like.

It is to be understood that the above-described device embodiments are illustrative of only a few of the many possible specific embodiments, based upon the intercalation of nanoparticles containing rare earth ions bound by an electrically insulating shell, within a one dimensional (1D) material nanoarchitecture used to collect and transport the radiation generated charges. Numerous and varied rare earth-based material compositions (composition, crystallinity, structure), and numerous a one dimensional (1D) semiconductor material nanoarchitectures (composition, crystallinity, structure) can be readily devised in accordance with the presented principles by those skilled in the art which are to be considered within the spirit and scope of the invention.

Use of Photocatalytic Devices for Photoconversion of $CO_2$ to Fuel

In yet a further aspect, a method for photocatalytically converting carbon dioxide into useful reaction products comprises introducing a reactant gas such as carbon dioxide alone, mixtures of carbon dioxide and hydrogen-containing gases such as water vapor, carbon dioxide and hydrogen, and mixtures of carbon dioxide with hydrogen-containing gases such as water vapor and other reactants as may be present or desirable such as fossil fuel derived products, into a reaction chamber in the presence of any one or more of the photocatalysts disclosed herein and in the presence of radiation to generate reaction products in the form of, for example, hydrocarbons, hydrogen, carbon monoxide, mixtures thereof, and other products as may be present or desirable.

Any one or more of the photocatalysts such as those described above may be used alone or in combination to effect photocatalytic conversion of any one or more of carbon dioxide alone, mixtures of carbon dioxide and hydrogen-containing gases such as water vapor, and mixtures of carbon dioxide, hydrogen-containing gases such as water vapor and other reactants as may be present or desirable to generate reaction products in the form of, for example, hydrocarbons, hydrogen, carbon monoxide, mixtures thereof, and other products as may be present or desirable. Hydrocarbon reaction products may include but are not limited to alkanes such as methane, ethane, propane, butane, pentane, hexane and mixtures thereof, olefins such as ethylene, propylene, butylene, pentene, hexane or mixtures thereof, and branched paraffins such as isobutene, 2,2-dimethyl propane, 2-methyl butane, 2,2-dimethyl butane, 2-methyl pentane, 3-methyl pentane and mixtures thereof. The reaction products may be further processed and refined to yield hydrogen-based fuels and other products, synthesis gas ("syngas") and derivatives of syngas (which may include hydrocarbon-based fuels and other products), and the like.

Batch processing, continuous flow-through processing, or combinations thereof may perform the methods disclosed herein for photocatalytic conversion. Both batch and continuous flow-through processes may be employed with gaseous carbon dioxide sources as well as supercritical carbon dioxide sources. Where open-ended flow-through type devices are employed they may be physically supported, for example, without limitation, on a mesh screen or the like, and may be planar or may be cylindrically shaped or in any other geometry or configuration as may be desired for different applications. The photocatalytic devices may be fabricated such that where electrons are made available to react with passing gas molecules is spatially separated from where holes are made available to react with passing gas molecules.

Photocatalytic conversion of an input reactant gas, such as any one or more of carbon dioxide alone, mixtures of carbon dioxide and hydrogen-containing gases such as water vapor, and mixtures of carbon dioxide, hydrogen-containing gases such as water vapor and other reactants as may be present or desirable, may be performed by admitting the input reactant gas into a reaction cell in the presence of one or more photocatalysts while admitting radiation into the reaction cell. Reaction cells for use in such manner generally include one or more inlets and outlets for admitting input gases into the cell and a window for admitting radiation, such as sunlight, into the cell. Input gases may be admitted as a mixture or may be admitted independently for mixing within the reaction cell. Preferably, the input reactant gases may be admitted as a mixture of carbon dioxide and hydrogen-containing gases such as water vapor.

Concentrators such as lenses, mirrors and the like, and/or other conventional optical devices and methods, may be used to distribute, separate, and/or increase the intensity of the radiation onto the photocatalyst present in the cell to enable use of higher input flow rates of the reactant gas(es) to enable increased generation rates of reaction products. The reaction products generated in conversion of mixtures of input gases may be analyzed by known methods such as gas chromatography equipped with flame ionization, pulsed discharge helium ionization, and thermal conductivity detectors.

What is claimed is:

1. A device for conversion of electromagnetic radiation into charges that are collected and used to promote chemical reactions comprising a rare earth ion containing material, the rare earth ion containing material comprising rare earth ions within crystallites, quantum-dots, and/or nanoparticles; the rare earth ion containing material is intercalated within a one-dimensional (1D) nanoarchitecture, wherein the chemical reactions comprise water-splitting and/or reduction of carbon dioxide, wherein the crystallites, quantum dots, or nanoparticles are comprised of one or more of the following elements lanthanum, cerium, praseodymium, neodymium, promethium, samarium, europium, gadolinium, terbium, dysprosium, holmium, erbium, thulium, ytterbium, lutetium, scandium, or yttrium.

2. The device of claim 1 wherein the crystallites, quantum dots, or nanoparticles containing the rare earth ions are bound within an organic host matrix comprising organic ligands bearing aromatic chromophores.

3. The device of claim 1 wherein the rare earth ions of the rare earth ion containing material are bound within an inorganic host matrix, the matrix comprising halides, oxides, oxyhalides, or oxysulfides.

4. The device of claim 1 wherein the radiation absorbed by the rare earth ion containing material possesses a wavelength from between 0.01 µm and 300 cm.

5. The device of claim 1 wherein the one dimensional (1D) material nanoarchitecture is an ordered array of one or more charge-transporting architectural features, the features selected from nanowires, nanotubes, nanorods, or nanofeathers.

6. The device of claim 1 wherein the one-dimensional (1D) nanoarchitecture comprises a plurality of elements, the elements being selected from nanowires, nanorods, nanotubes or nanofeathers wherein the feature to feature spacing of the elements is less than 4 µm and length of the elements is more than 50 nm and less than 100 mm.

7. The device of claim 1 wherein the 1D material nanoarchitecture is made of one or more semiconductors.

8. The device of claim 1 wherein the rare earth ion containing nanoparticles or quantum dots are intercalated within the one (1D) material nanoarchitecture using sol-gel, potential-assisted sol-gel, electrodeposition, photodeposition, centrifuge-assisted deposition, microemulsion, spin-coating, atomic layer deposition, hydrothermal synthesis, microwave-assisted hydrothermal synthesis, or dip-coating techniques.

9. The device of claim 1 wherein the crystallites, quantum dots, or nanoparticles containing rare earth ions are in contact with compounds including, but not limited to, graphene, graphene oxide, or boron nitride, by which charge separation is facilitated.

10. The device of claim 1 wherein the rare earth ion containing crystallites, quantum dots, or nanoparticles contain one or more nonmetals selected from the group consisting of B, C, K, Ca, Na, F, I, P, S or mixtures thereof.

11. A method for photocatalytically converting carbon dioxide into reaction products comprising any one or more of hydrocarbons and hydrocarbon-containing products, hydrogen and hydrogen-containing products, carbon monoxide and carbon-containing products, or combinations thereof, comprising exposing a reactant gas comprising carbon dioxide to the device of claim 1 and electromagnetic radiation to generate the reaction products, wherein the rare earth ion containing photocatalytic device is in the form of a flow-through membrane.

12. The method of claim 11, where the electromagnetic radiation comprises ultraviolet, visible, infrared radiation, millimeter wave, microwave, or any combination thereof.

13. A method for photocatalytically converting a first gas into reaction products comprising any one or more other gases, or combinations thereof, comprising exposing a reactant gas comprised at least in part of the first gas to the device of claim 1 and electromagnetic radiation to generate the reaction products.

14. A device for conversion of electromagnetic radiation into charges that are collected and used to promote chemical reactions comprising a rare earth ion containing material, the rare earth ion containing material comprising rare earth ions within crystallites, quantum-dots, and/or nanoparticles; the rare earth ion containing material is intercalated within a one-dimensional (1D) nanoarchitecture, wherein the chemical reactions comprise water-splitting and/or reduction of carbon dioxide, wherein the charge generation capabilities of the rare earth ion containing crystallites, quantum dots, or nanoparticles are adjusted through appropriate elemental doping.

15. A device for conversion of electromagnetic radiation into charges that are collected and used to promote chemical reactions comprising a rare earth ion containing material, the rare earth ion containing material comprising rare earth ions within crystallites, quantum-dots, and/or nanoparticles; the rare earth ion containing material is intercalated within a one-dimensional (1D) nanoarchitecture, wherein the chemical reactions comprise water-splitting and/or reduction of carbon dioxide, wherein crystallites, quantum dots, or nanoparticles of one or more co-catalysts are deposited on one or more surfaces of the device wherein the co-catalyst is selected from the group consisting of graphene, boron nitride, Ag, As, Au, Bi, Cd, Co, Cu, CuO, Cu2O, Fe, Ga, Ge, In, Ir, Ni, Pb, Pd, Pt, Rh, Sb, Si, Sn, Ta, TI, W, Zn or mixtures thereof.

16. A device for conversion of electromagnetic radiation into charges that are collected and used to promote chemical reactions comprising a rare earth ion containing material, the rare earth ion containing material comprising rare earth ions within crystallites, quantum-dots, and/or nanoparticles; the rare earth ion containing material is intercalated within a one-dimensional (1D) nanoarchitecture, wherein the chemical reactions comprise water-splitting and/or reduction of carbon dioxide, wherein the one-dimensional structure is a p-type semiconductor, and in contact with an underlying p-type semiconductor substrate, so that holes within the one-dimensional structure may pass into the underlying p-type semiconductor substrate and thereby react with gas molecules at a distance from the one-dimensional structures.

17. The device of claim 16 wherein the underlying substrate is a conductor.

18. A device for conversion of electromagnetic radiation into charges that are collected and used to promote chemical reactions comprising a rare earth ion containing material, the rare earth ion containing material comprising rare earth ions within crystallites, quantum-dots, and/or nanoparticles; the rare earth ion containing material is intercalated within a one-dimensional (1D) nanoarchitecture, wherein the chemical reactions comprise water-splitting and/or reduction of carbon dioxide, wherein the one-dimensional structure is a n-type semiconductor, and in contact with an underlying n-type semiconductor substrate, so that holes within the one-dimensional structure may pass into the substrate and thereby react with gas molecules at a distance from the one-dimensional structures.

\* \* \* \* \*